(12) United States Patent
Choudhury et al.

(10) Patent No.: US 9,814,631 B2
(45) Date of Patent: Nov. 14, 2017

(54) CONTAINER FOR SURGICAL ABSORBENT ARTICLES

(71) Applicants: Sambhu Choudhury, Cincinnati, OH (US); Sean Lynch, Cincinnati, OH (US); Arturo David Sanchez, Cincinnati, OH (US)

(72) Inventors: Sambhu Choudhury, Cincinnati, OH (US); Sean Lynch, Cincinnati, OH (US); Arturo David Sanchez, Cincinnati, OH (US)

( * ) Notice: Subject to any disclaimer, the term of this patent is extended or adjusted under 35 U.S.C. 154(b) by 0 days.

(21) Appl. No.: 14/636,748

(22) Filed: Mar. 3, 2015

(65) Prior Publication Data
US 2015/0245955 A1    Sep. 3, 2015

Related U.S. Application Data

(60) Provisional application No. 61/947,137, filed on Mar. 3, 2014.

(51) Int. Cl.
| | |
|---|---|
| A61B 17/06 | (2006.01) |
| A61B 19/02 | (2006.01) |
| A61L 15/00 | (2006.01) |
| A61F 13/36 | (2006.01) |
| A61F 15/00 | (2006.01) |
| A61F 13/44 | (2006.01) |
| A61B 50/10 | (2016.01) |
| A61B 50/20 | (2016.01) |
| A61B 50/30 | (2016.01) |
| A61B 90/98 | (2016.01) |
| A61B 50/00 | (2016.01) |
| A61B 90/00 | (2016.01) |

(52) U.S. Cl.
CPC ............ *A61F 13/36* (2013.01); *A61B 50/10* (2016.02); *A61B 50/20* (2016.02); *A61B 50/30* (2016.02); *A61B 90/98* (2016.02); *A61F 13/44* (2013.01); *A61F 15/001* (2013.01); *A61B 2050/0059* (2016.02); *A61B 2050/3008* (2016.02); *A61B 2090/3966* (2016.02)

(58) Field of Classification Search
CPC ...... A61F 13/36; A61F 15/001; A61F 2/0095; A61F 13/44; A61B 19/02; A61B 19/026; A61B 90/98; A61L 2/26
USPC ....... 206/438, 440, 363, 210, 223, 570, 571, 206/233, 745, 205, 207, 494, 366; 222/94; 221/92, 102, 131, 34, 35
See application file for complete search history.

(56) References Cited

U.S. PATENT DOCUMENTS

| | | | | |
|---|---|---|---|---|
| 4,190,153 | A | * | 2/1980 | Olsen ................. A61B 19/029 206/362 |
| 4,429,789 | A | * | 2/1984 | Puckett, Jr. .......... A61B 19/029 206/370 |
| 4,943,939 | A | * | 7/1990 | Hoover .............. A61B 19/0256 206/363 |

(Continued)

*Primary Examiner* — J. Gregory Pickett
*Assistant Examiner* — Rafael Ortiz
(74) *Attorney, Agent, or Firm* — Jenei LLC

(57) ABSTRACT

A surgical container has more than one surgical sponge, more than one dispensing containers containing respectively the more than one surgical sponge, and more than one disposal containers each proximate to and visually associated respectively with the more than one dispensing containers to receive a used surgical sponge, wherein a selected surgical sponge is visible in one of the dispensing container or the corresponding disposal container.

16 Claims, 6 Drawing Sheets

(56) References Cited

U.S. PATENT DOCUMENTS

| | | | | |
|---|---|---|---|---|
| 5,957,325 | A * | 9/1999 | Montanez | A47F 1/08 |
| | | | | 221/131 |
| 2004/0040873 | A1 * | 3/2004 | Koseki | A61B 19/0288 |
| | | | | 206/363 |
| 2005/0178783 | A1 * | 8/2005 | Pastan | A61F 15/001 |
| | | | | 221/58 |
| 2008/0030303 | A1 * | 2/2008 | Kobren | A61F 13/36 |
| | | | | 340/5.92 |
| 2009/0223992 | A1 * | 9/2009 | Lorenzati | A47K 10/421 |
| | | | | 221/34 |
| 2011/0223255 | A1 * | 9/2011 | Thiesen | A61K 9/0024 |
| | | | | 424/489 |
| 2015/0150736 | A1 * | 6/2015 | Pierre | A61F 15/001 |
| | | | | 206/440 |

\* cited by examiner

CONTAINER FOR SURGICAL ABSORBENT ARTICLES

CROSS-REFERENCE TO RELATED APPLICATION

This application claims priority or the benefit of U.S. Provisional Application 61/947,137, filed Mar. 3, 2014, the contents of which are fully incorporated herein by reference.

BACKGROUND OF THE INVENTION

1. Field of the Invention

The field of art disclosed herein pertains to surgical containers for absorbent articles such as sponges or gauzes, and more particularly to surgical containers for tracking disposition of unused and used absorbent articles.

2. Description of the Related Art

Surgical procedures require use of absorbent articles such as sponges and gauze in order to collect bodily fluids. Maintaining sterile conditions for unused absorbent articles is one consideration. Another requirement is that used absorbent articles be properly disposed of to mitigate biohazards. Another consideration is that all used absorbent articles should be accounted for before finishing the surgical procedure. Leaving used absorbent articles in a body cavity of a patient may cause serious risks to health as well as unacceptable consequences to those responsible.

SUMMARY OF THE INVENTION

In one aspect, the present disclosure provides a surgical container that has more than one surgical sponge, more than one dispensing containers containing respectively the more than one surgical sponge, and more than one disposal containers each proximate to and visually associated respectively with the more than one dispensing containers to receive a used surgical sponge, wherein a selected surgical sponge is visible in one of the dispensing container or the corresponding disposal container.

These and other features are explained more fully in the embodiments illustrated below. It should be understood that in general the features of one embodiment also may be used in combination with features of another embodiment and that the embodiments are not intended to limit the scope of the invention.

BRIEF DESCRIPTION OF THE DRAWINGS

The various exemplary embodiments of the present invention, which will become more apparent as the description proceeds, are described in the following detailed description in conjunction with the accompanying drawings, in which.

DETAILED DESCRIPTION

Figure 1:
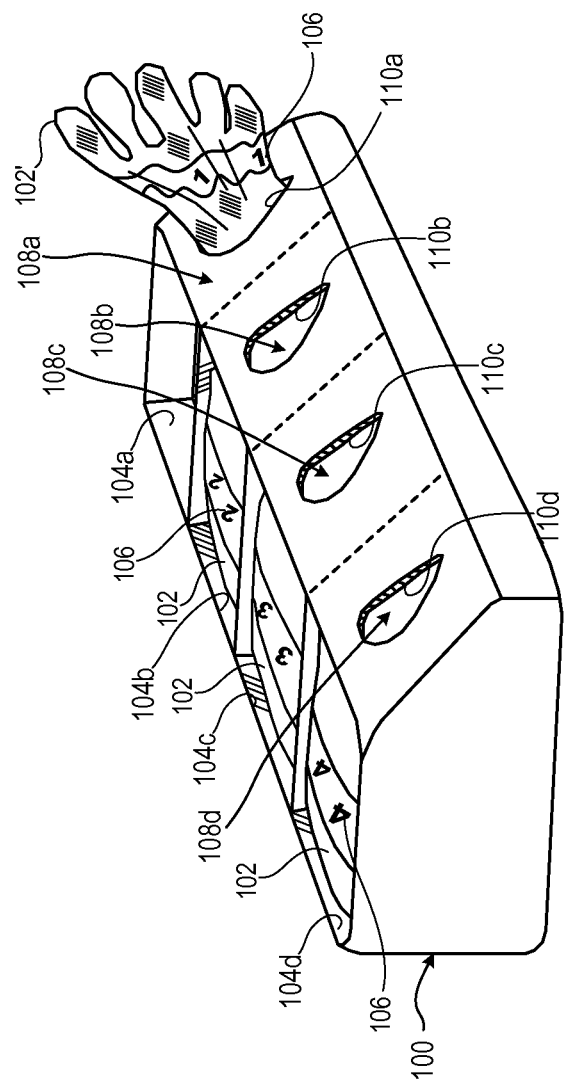
FIG. 1 illustrates an isometric view of a first example container for dispensing unused absorbent articles and for visibly disposing of used absorbent articles, according to one embodiment.

The present invention involves the use of materials and methods for surgical sponges and related medical devices, which will be used to identify and track those sponges during surgery.

The sponge count is an essential part of operating room procedure. The present invention will increase the accuracy of sponge counts by eliminating human error and providing a running count of sponges already used. This is important because it allows the staff to constantly check counts throughout the procedure. An increase in accuracy reduces the chances that a sponge will be left in a patient. This increases safety for the patient and reduces the time that is spent recounting sponges, thus reducing total count time.

The present innovation relates generally to a surgical container that has more than one surgical sponge, more than one dispensing containers containing respectively the more than one surgical sponge, and more than one disposal containers each proximate to and visually associated respectively with the more than one dispensing containers to receive a used surgical sponge, wherein a selected surgical sponge is visible in one of the dispensing container or the corresponding disposal container.

Detailed descriptions of well-known sponge material, methods of attaching or incorporating a marker, manufacturing methods, and methods of packaging are omitted so as not to obscure the description of the present invention. In addition, as will be evident to those skilled in the art, the present invention could be used in place of, or in conjunction with, the currently available surgical pads and sponges, including laparotomy pads.

In one embodiment, the sponge management system of the present invention provides for individual sponges to be segmented into compartments like an egg carton. However, the carton has a double chamber—a second one below or adjacent to the first—wherein there is a keyhole between the two compartments. After use, the used sponge is pushed through the keyhole (or v-shaped) into deeper chamber. The used sponge may be hooked into keyhole slot to hang over side and remain visible. The sponges may be labeled with a color-coordinated segment and number so that the count is easily verified. In one embodiment, each pack is a specific color such that one pack is one color e.g., red #1, red #2,red #3, etc., and another pack is another color such as blue #1, blue #2,blue #3, etc. In one embodiment, a system is provided such that a variety of surgical sponge packs are provided wherein each pack has a unique color coding so that as the labeled sponges are disposed of, only the coordinating color sponges are placed in the pack compartments.

In one embodiment, the disposal compartment of the container is sized appropriately such that the volume of the disposal compartment is large enough to contain only a single sponge so that two sponges cannot inadvertently be placed into a single, disposal compartment.

In one embodiment, individual sponges are segmented into compartments like an egg carton. However, the carton has a double chamber—a second one in front of the first—wherein there is a keyhole slot opening to the second compartment adjacent for immediate disposal after use. After use, the used sponge is pushed through the keyhole (or v-shaped) into second compartment but the used sponge is hooked into keyhole slot to hang over side and remain visible.

In one embodiment, the sponges are labeled with a color-coordinated segment and number so that the count is easily verified. In one embodiment, each pack is a specific color e.g., red 1, red 2, etc., blue 1, blue 2, etc. or red A, red B, etc. In another embodiment, different colors are used to indicate different types of sponges. The ability to distinguish between different types of sponges helps to accurately estimate the amount of blood lost during surgery. For example, Raytec sponges weigh, when dry, about five grams. Lap sponges weigh, when dry, about 20 grams. When soaked with blood and/or other bodily fluids, Raytec sponges can weigh up to about 50 grams and Lap sponges can weigh up to about 120 grams.

Turning to the drawings, wherein like numerals represent like components throughout the several view, FIG. 1 illustrates a first example container 100 for dispensing unused absorbent articles 102 such as surgical sponges, gauzes, towels, etc., and for visibly disposing of used absorbent articles 102', according to one embodiment. For clarity, one rows of four dispensing container 104a-104d are depicted, although more rows, rows of different numbers or letters, and orientations other than straight may be used consistent with aspects of the present disclosure. To assist in tracking, each unused absorbent article 102 that may eventually become a used absorbent article 102' is labeled with a sequential indicium 106 (e.g., number, alphabet letter, color, etc.) that assists in disposing of the then used absorbent article 102 in a visually associated and corresponding disposal container 108a-108d that is proximate respectively to the dispensing container 104a-104s. Apertures 110a-110d respectively in the disposal containers 108a-108d may be a slit, teardrop, or other shape that may grip for exposure of the sequential indicium 106 for tracking purposes.

Figure 2:
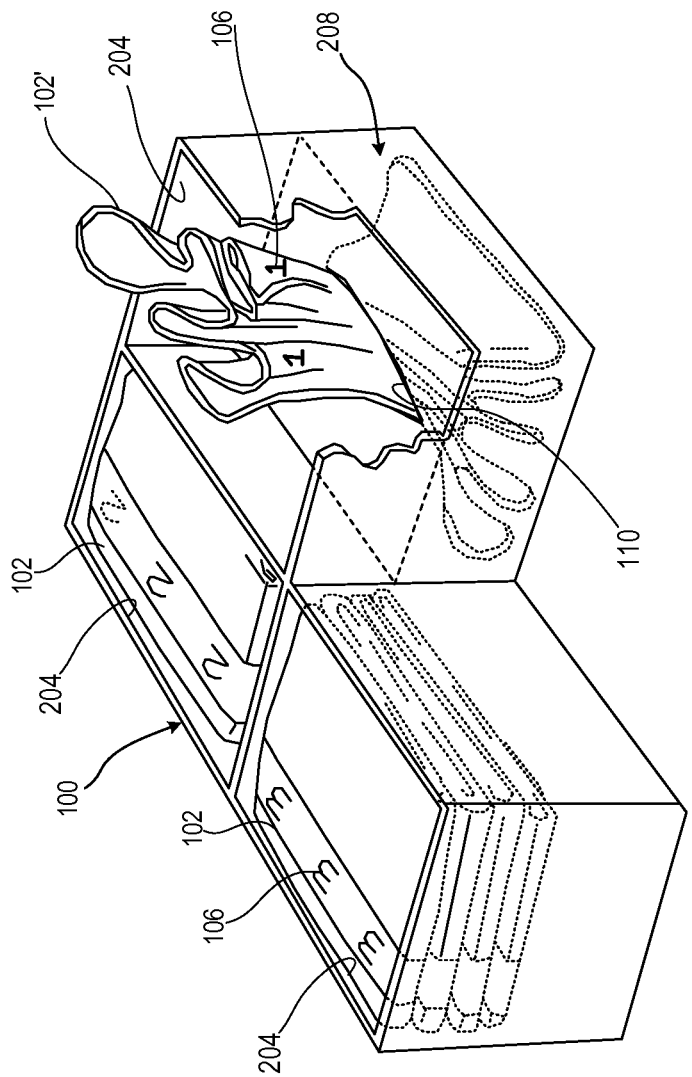
FIG. 2 illustrates an isometric view of a portion of a second example container for dispensing unused absorbent articles and for visibly disposing of used absorbent articles, according to one embodiment.
Figure 3:
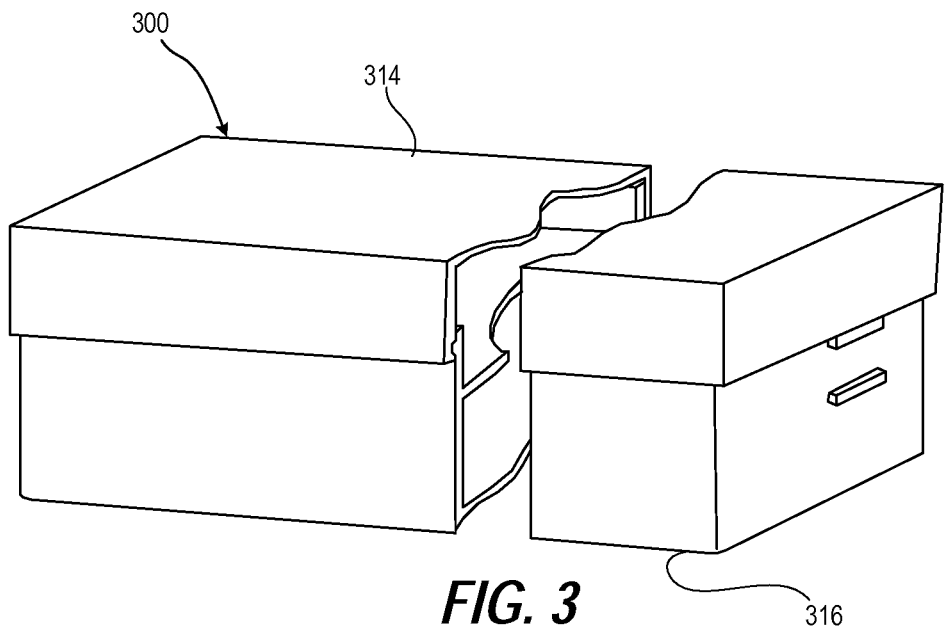
FIG. 3 illustrates an isometric, partially cutaway view of a lidded, stacked and angled container for dispensing unused absorbent articles and for visibly disposing of used absorbent articles, according to one embodiment.
Figure 4:
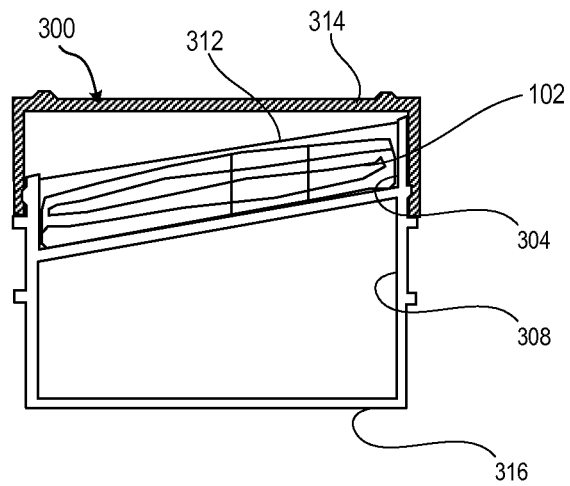
FIG. 4 illustrates a side view in vertical cross section of the lidded, stacked and angled container of FIG. 3, according to one embodiment.
Figure 5:
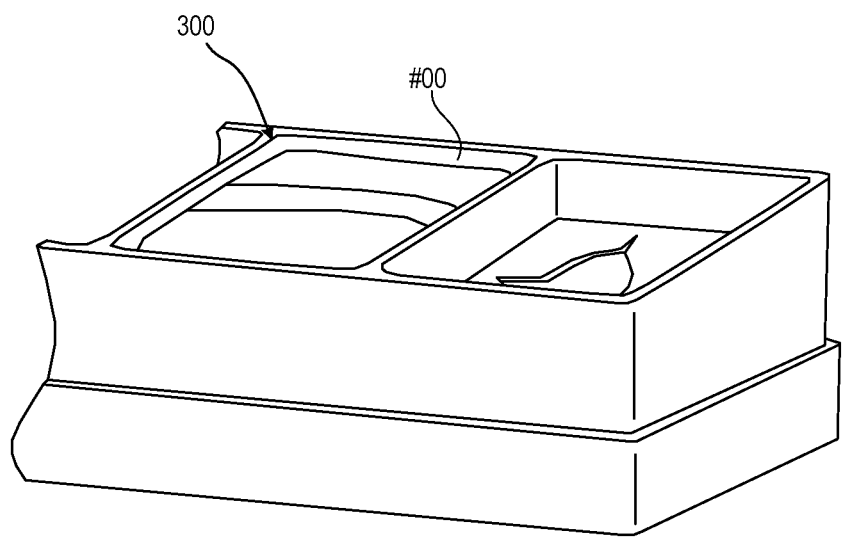
FIG. 5 illustrates an isometric, partially cutaway view of the lidded, stacked and angled container of FIG. 3 with a top lid stowed underneath as an antiskid surface, according to one embodiment.
Figure 6:
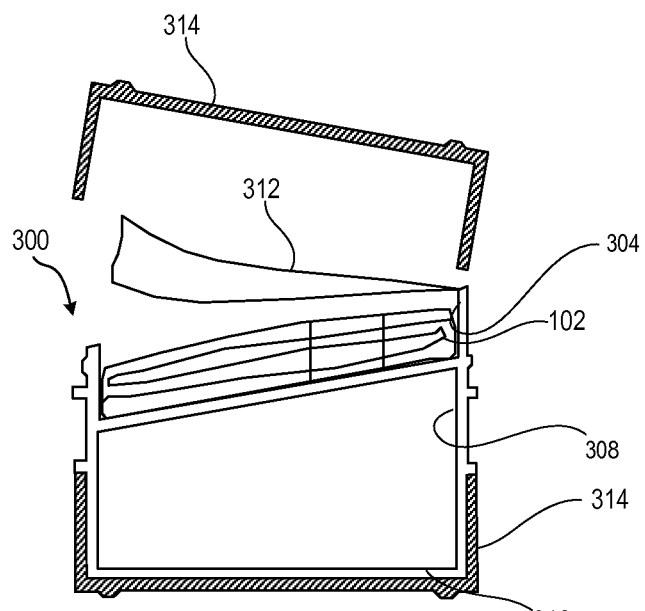
FIG. 6 illustrates a side view in vertical cross section of the angled container of FIG. 5 with the lid stowed, according to one embodiment.

FIG. 2 illustrates a second example container 200 for dispensing unused absorbent articles 102 and for visibly disposing of used absorbent articles 102' wherein each dispenser container 204 is positioned above the corresponding disposal container 208.

FIGS. 3-6 illustrate a lidded, stacked and angled surgical container 300 for dispensing unused absorbent articles 102 and for visibly disposing of used absorbent articles 102'. The surgical container 300 has more than one dispenser containers 304 are inclined toward an orientation of a user and are above corresponding disposal containers 308. The container 100 may comprise transparent material to expose contents of each disposal container 308. A transparent sterile membrane 312 encloses each dispensing container 304. A lid 314 is sized to enclose the more than one dispensing container 304 and to be received on a bottom 316 of the surgical container 300 until needed to close the container 300 after use or to provide a slip resistant surface.

Figure 7:
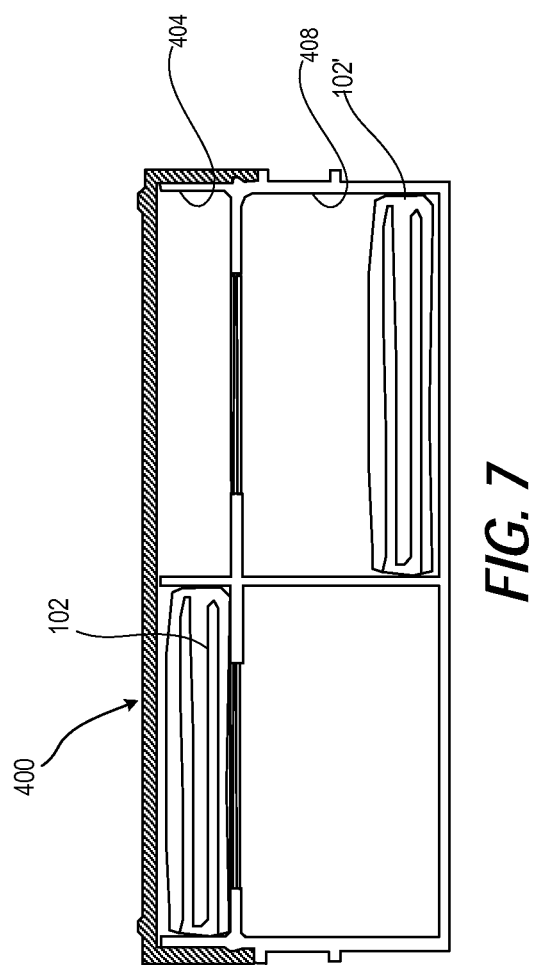
FIG. 7 illustrates a side view in vertical cross section of an alternate lidded, stacked and horizontal container, according to one embodiment.

FIG. 7 illustrates an alternate lidded, stacked and horizontal container 400 having horizontal dispensing containers 404 overtop of corresponding disposal containers 408 for managing unused and used absorbent articles 102, 102'.

Figure 8:
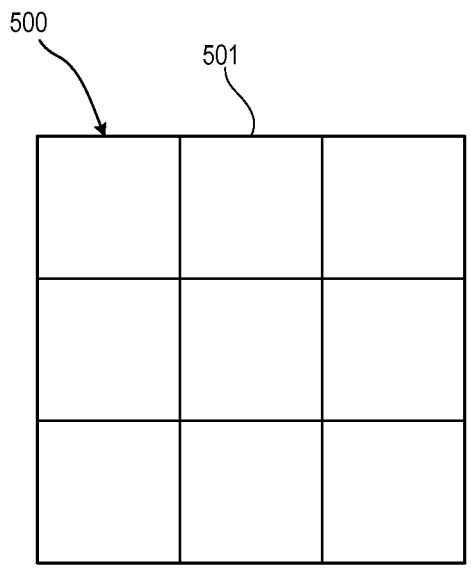
FIG. 8 illustrates a diagram of a 3×3 arrangement of a stacked container, according to one embodiment.

FIG. 8 illustrates a portion of a 3×3 stacked container 500 of trays 501, according to one embodiment.

Figure 9:
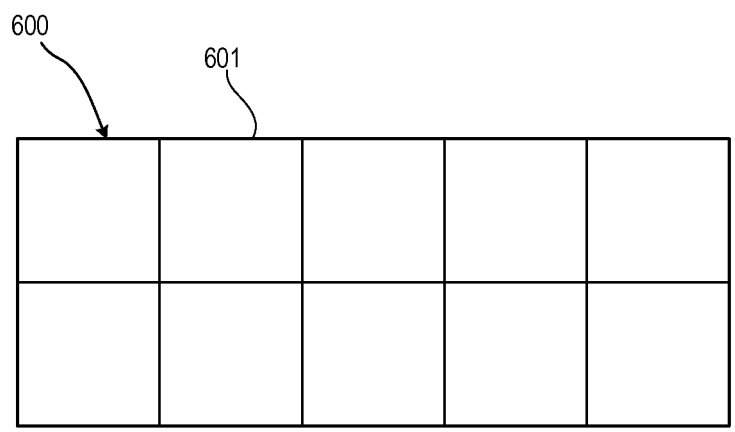
FIG. 9 illustrates a diagram of a 2×5 arrangement of a stacked container, according to one embodiment.

FIG. 9 illustrates a portion of a 2×5 stacked container 600 of trays 601, according to one embodiment.

An absorbent article 102 such as a surgical sponge is provided and adapted to prevent unaccounted disposal thereof. The sponge includes an absorbent pad and a visually identifiable member attached to the pad. The visually identifiable member assists in identification and accounting in a surgical environment. In another embodiment, an additional a tag of sufficient size is incorporated with the sponge to provide detection by a metal detector device upon disposal of the sponge.

Referring now to FIG. 2, an absorbent article 102 is illustrated and includes an absorbent pad that is labeled with a sequential indicium 106 (e.g., number, alphabet letter, color, etc.). The sequential indicium 106 may be attached to the absorbent article 102 in any manner that makes the sequential indicium 106 visually identifiable.

In one embodiment, the absorbent article 102 is color-coded in a color contrasting with the colors typically found in a body cavity of a patient. Such colors may include blue, yellow, orange, lavender, green and the like. This provides two primary benefits. First, when the absorbent article 102 is placed within the body cavity of a patient, for example, so that the absorbent article 102 becomes absorbed in blood and other bodily fluids, the color of the absorbent article 102 and/or sequential indicium 106 can still be readily seen since it is contrasted with the fluid and tissue colors of the patient. Moreover, the colors utilized with the absorbent article 102 and/or sequential indicium 106 may also be color matched or coordinated to the box container or other holder to permit easy counting to determine the absence of any absorbent article 102 after the surgery is complete.

In other embodiments, the material of the absorbent article 102 itself is color-coded in a color. In other embodiments, the sequential indicium 106 of the absorbent article 102 is color-coded in a color. In other embodiments, both the absorbent article 102 itself and the sequential indicium 106 of the absorbent article 102 are color-coded in a color.

However, mere color coding of tagged or other identifying elements associated with the absorbent article 102 by itself may still be insufficient. This is due to the fact that while the color contrast may make the sponges easier to identify within the body cavity of a patient, the proper number of sponges must be counted in order to indicate a lack of accounting of all the sponges. To obviate the above problem without using expensive active sensors, the absorbent article 102 of the present invention optionally includes a number tag as part of the sequential indicium 106 associated with the visually identifiable absorbent article 102.

In one embodiment, the sponge is made of an absorbent material and further comprises a radio-opaque material, wherein the radio-opaque material is incorporated into the absorbent material.

The absorbent article 102 can be of any desired thickness, and in one embodiment is in the range of about 1 to about 5 millimeters in thickness, which is sufficient for fluid absorption, possesses adequate permeability for use with fluid suction devices, and is sufficiently pliable to serve as a tissue wipe.

In one embodiment, the sponge has the material enhancing the adherence of the sponge to the applied tissue in the form of a continuous or discontinuous layer on at least one surface of the sponge.

In one embodiment, the sponge of the present invention has an overall thickness of less than 5 mm. In another embodiment, the sponge has an overall thickness of less than 3 mm. In another embodiment, the sponge has an overall thickness of about 1 mm to about 3 mm.

The sponge may further comprise an activator or proactivator of blood coagulation, including fibrinogen, thrombin or a thrombin precursor, as e.g. disclosed in U.S. Pat. No. 5,714,370 (incorporated herein by reference). In the following thrombin activity is understood to comprise both, the activity of thrombin or any equivalent activity. A protein with thrombin activity might be selected from the group consisting of alpha-thrombin, meizothrombin, a thrombin derivative or a recombinant thrombin. A suitable precursor is possibly selected from the group consisting of: prothrombin, factor Xa optionally together with phospholipids, factor IXa, activated prothrombin complex, FEIBA, any activator or a proactivator of the intrinsic or extrinsic coagulation, or mixtures thereof.

The sponge according to the invention can optionally be used together with further physiologic substances. For example, the sponge optionally further comprises pharmacologically active substances, among them antifibrinolytics, such as a plasminogenactivator-inhibitor or a plasmin inhibitor or an inactivator of fibrinolytics. A preferred antifibrinolytic is selected from the group consisting of aprotinin or an aprotinin derivative, alpha2-macroglobulin, an inhibitor or inactivator of protein C or activated protein C, a substrate mimic binding to plasmin that acts competitively with natural substrates, and an antibody inhibiting fibrinolytic activity.

In one embodiment, the further pharmacologically active substance is an antibiotic, such as an antibacterial or antimycotic. Further bioactive substances such as growth factors and/or pain killers may be also present in the inventive sponge. Such a sponge might be useful in e.g. wound healing.

Further combinations are useful with specific enzymes or enzyme inhibitors, which may regulate, i.e. accelerate or inhibit, the resorption of the sponge. Among those are collagenase, its enhancers or inhibitors. Also, a suitable preservative may be used together with the sponge or may be contained in the sponge.

In one embodiment, the absorbent article 102 is constructed from an absorbent material (cotton) comprising a plurality of layers of open mesh gauze. As is well-known in the art, the gauze is preferably woven in a weave pattern suitable for use both as a drape in a surgical procedure and in the nature of a laparotomy sponge. Alternately, the absorbent article 102 could be constructed of a nonwoven material. The nonwoven fabric may comprise any suitable combination of natural and/or synthetic textile materials including cotton, rayon, acrylics, polyester and nylon.

A surgical sponge in accordance with the present invention may be fabricated by weaving polymer filaments into a sheet and cutting appropriately dimensioned pledgets therefrom. The sponge, though shown in the shape of a sheet pad, may be formed in any desired and sensible shape.

In another embodiment, the sponge is comprised of a bioabsorbable material formed into a body having a plurality of interconnecting pores that open to the surface of the sponge. The bioabsorbable material may be a fibrous mass of bioabsorbable filaments or it may be a bioabsorbable "open cell" foam body. The biodegradable material used for the construction of the sponge should preferably have a hydrophilic outer surface to facilitate the absorbtion of blood into the sponge. Suitable biodegradable materials for fabricating the surgical sponge include filaments or foam bodies comprised of polymers or copolymers of lactide, glycolide, caprolactone, polydioxanone, trimethylene carbonate, polyorthoesters and polyethylene oxide, collagen and high molecular weight polysaccharides from connective tissue such as chondroitin salts. Other polysaccharides that can be formed into a porous body may also prove suitable, such as chitin and chitosan. Additional bioabsorbable materials are in intense development and it is expected that many of the new materials will also be applicable for forming a biodegradable surgical sponge in accordance with the present invention.

The sponges of the present invention may be sterilized by heat, ethylene oxide or radiation, the choice depending on the sponge material selected.

In a still further embodiment of the invention, the sponge is provided in combination with a high radiographic density and a high effective area for an x-ray beam incident thereon at any orientation.

In a still further embodiment of the invention, the sponge container is marked in an area on the outer surface. In one embodiment, the sponge container may be marked in an area on the outer surface with a before and after weight that enables a person to weigh the container to see the additional weight added after the sponges are used to compare with the original dry sponges, in single or stacked containers, to obtain a more accurate estimate of blood loss during surgery. Alternatively, the container comprises a transparent material to permit a doctor to visually inspect the blood-soaked sponges confined in their containers to assess the blood loss.

In a still further embodiment of the invention, the main part of the sponge container is a single compartment formed from a transparent, semi-rigid, thermoplastic material on a packaging machine to hold clean surgical sponges.

In a further aspect of the invention, the surgical sponge comprises in combination a radiographic marker and a remotely detectable electronic article surveillance tag. Such a sponge advantageously may be detected by the electronic means and removed from the patient prior to completion of surgery. However, even if the sponge is inadvertently not detected and removed, the marker further enhances the detectability of the present sponge in comparison to sponges bearing previously known radiopaque elements.

In a further aspect of the invention, the surgical sponge provides a radiopaque marker suitable for association with a surgical sponge or other surgical implement. The marker has a high radiographic density and a distinctive shape, whereby the marker produces an x-ray image with high contrast and a shape that is readily recognizable and differentiated from the images produced by other items and structures commonly seen in x-rays of post-operative patients. The marker is suitable for association with a surgical sponge and has an x-ray density equivalent to at least about 0.1 g/cm2 of $BaSO_4$.

The marked surgical sponge of the invention may be used in conjunction with any remotely detectable electronic article surveillance (EAS) tag system capable of sensing and remotely detecting an EAS tag and compatible with the requirements of safe operation in the context of a medical venue. A wide variety of such EAS systems are currently known, including microwave, RF, and magnetic systems. Some of these systems employ substantially identical tags, so that the system simply indicates the presence or absence of a tag. Other systems have now become available in which each tag has a unique signature that is remotely recognizable by the detection system. One such system is the magneto-mechanically actuated article surveillance system disclosed by U.S. Pat. Nos. 4,510,489 and 4,510,490. Another system is the harmonic-responsive article surveillance system disclosed by U.S. Pat. RE 35,042.

Many tags suitable for use in the practice of the present invention comprise an active electronic receptor element that is encased in a plastic housing comprising some means allowing the tag to be attached to another item. The term "tag" is used herein to refer generically to the combination of the active element and any housing or related mounting means. In addition, it will be understood that a tag may include more than one active element, which elements may be responsive to EAS systems of different types. It will also be appreciated that more than one tag may be attached to a given surgical item to further improve its detectability or to allow detection by EAS systems of different types. In one embodiment, the tags can endure temperatures of up to about 400 degrees Fahrenheit (about 200 degrees Centigrade) to allow them to be autoclaved.

It must be noted that, as used in this specification and the appended claims, the singular forms "a," "an" and "the" include plural referents unless the content clearly dictates otherwise. Thus, for example, reference to a "colorant agent" includes two or more such agents.

Unless defined otherwise, all technical and scientific terms used herein have the same meaning as commonly understood by one of ordinary skill in the art to which the invention pertains. Although a number of methods and materials similar or equivalent to those described herein can be used in the practice of the present invention, the preferred materials and methods are described herein.

As will be appreciated by one having ordinary skill in the art, the methods and compositions of the invention substantially reduce or eliminate the disadvantages and drawbacks associated with prior art methods and compositions.

It should be noted that, when employed in the present disclosure, the terms "comprises," "comprising," and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

While it is apparent that the illustrative embodiments of the invention herein disclosed fulfill the objectives stated above, it will be appreciated that numerous modifications and other embodiments may be devised by one of ordinary skill in the art. Accordingly, it will be understood that the appended claims are intended to cover all such modifications and embodiments, which come within the spirit and scope of the present invention.

What is claimed is:

1. A surgical container comprising:
   more than one surgical sponge;
   more than one dispensing containers containing respectively the more than one surgical sponge;
   more than one disposal containers each proximate to and visually associated respectively with the more than one dispensing containers to receive a used surgical sponge, wherein a selected surgical sponge is visible in one of the dispensing container or the corresponding disposal container, wherein the disposal container comprises an aperture to grip and expose a portion of a received used surgical sponge;
   a transparent sterile membrane that encloses each dispensing container; and
   a lid sized to enclose the more than one dispensing container and to be received on a bottom of the surgical container.

2. The surgical container of claim 1, wherein more than one disposal containers are inclined toward an orientation of a user.

3. The surgical container of claim 1, wherein each dispensing container is positioned adjacent to the corresponding disposal container.

4. The surgical container of claim 1, wherein the more than one surgical sponge are operable for the intraoperative absorption of blood from within an open surgical site within a patient, wherein each of the more than one surgical sponge comprises a porous body and a marker integrated within the surgical sponge, wherein the marker comprises an identifiable number and an identifiable color; wherein the marker is capable of functioning after enduring fluids, including blood and other bodily fluids.

5. The surgical item of claim 4 wherein the sponge is a laparotomy sponge.

6. The surgical item of claim 4 wherein the sponge includes a radio-opaque member.

7. The surgical item of claim 4 wherein the sponge comprises a bioabsorbable material.

8. The surgical item of claim 4 wherein the sponge has a thickness of about 1 to about 5 millimeters and is sufficient for fluid absorption.

9. The surgical container of claim 4 wherein the container and surgical sponges are coded with a specific color to denote a specific type of sponge contained within the container.

10. The surgical item of claim 4 wherein the sponge further comprises an activator or proactivator of blood coagulation.

11. The surgical item of claim 4 wherein the sponge further comprises a pharmacologically active substance.

12. The surgical item of claim 4 wherein the sponge further comprises a second marker.

13. The surgical item of claim 12 wherein the second marker is a second identifiable color.

14. The surgical item of claim 12 wherein the second marker is a remotely detectable electronic article surveillance (EAS) tag system.

15. The surgical container of claim 1, further comprising a surgical item operable for the intraoperative absorption of blood from within an open surgical site within a patient, wherein the surgical item comprises a sponge having a porous body and a marker integrated within the sponge, wherein the marker comprises a sequential indicium of an identifiable color; wherein the marker is capable of functioning after enduring fluids, including blood and other bodily fluids, wherein one of the dispensing and disposal containers comprise a respective corresponding color.

16. The surgical container of claim 1, wherein the dispensing containers, the surgical sponges, and the disposal containers each include a first specific color to be associated together as a first surgical container that differs from one or more other surgical containers having a respective specific color.

* * * * *